United States Patent [19]
Koskela

[11] Patent Number: 5,661,231
[45] Date of Patent: Aug. 26, 1997

[54] ARRANGEMENT FOR LEAK TESTING PLACE IN CONNECTION WITH A VENTILATOR

[75] Inventor: Hannu Koskela, Helsinki, Finland

[73] Assignee: Instrumentarium Oy, Finland

[21] Appl. No.: 617,323

[22] Filed: Mar. 18, 1996

[30] Foreign Application Priority Data

May 12, 1995 [FI] Finland ................................. 952343

[51] Int. Cl.[6] ........................................................ G01M 3/28
[52] U.S. Cl. ................................ 73/49.8; 73/40.5 R
[58] Field of Search ......................... 73/40, 49.8, 40.5 R; 128/202.22, 205.23, 204.18; 340/687

[56] References Cited

U.S. PATENT DOCUMENTS

| 3,595,228 | 7/1971 | Simon et al. ................ 128/202.22 |
| 3,923,056 | 12/1975 | Bingmann et al. . |
| 4,067,329 | 1/1978 | Winicki ......................... 128/202.22 |
| 5,235,973 | 8/1993 | Levinson . |

FOREIGN PATENT DOCUMENTS

| 346548 | 12/1989 | European Pat. Off. . |
| 2249728 | 5/1992 | United Kingdom ............ 128/202.22 |
| 90/03820 | 4/1990 | WIPO . |
| WO91/16937 | 11/1991 | WIPO ........................... 128/202.22 |
| 94/22516 | 10/1994 | WIPO . |

OTHER PUBLICATIONS

William W. Mushin et al.: *Automatic Ventilation of the Lungs*, 1980 Blackwell Scientific Publications, Oxford London Edinburgh Melbourne XP00202440 166160, p. 41, line 13 through p. 45, line 12; figure 2.7.

Primary Examiner—Michael Brock
Attorney, Agent, or Firm—Andrus, Sceales, Starke & Sawall

[57] ABSTRACT

An arrangement for leak testing an equipment consisting of a ventilator and of a breathing system provided between the ventilator and a patient, said ventilator comprising a gas delivery means and an expiration and inspiration valve, and said breathing system comprising at least tubing provided between the patient and the ventilator and a connector as well as possible other auxiliaries, the arrangement thus comprising a closing part, by means of which the connector can be closed during leak testing. To achieve automatic detection, the closing part is provided with a detecting means, which is arranged to provide a signal when the closing part closes the connector.

15 Claims, 3 Drawing Sheets

ARRANGEMENT FOR LEAK TESTING PLACE IN CONNECTION WITH A VENTILATOR

BACKGROUND OF THE INVENTION

The present invention relates to an arrangement for leak testing equipment consisting of a ventilator and of a breathing system provided between the ventilator and a patient, said ventilator comprising a gas delivery means and an expiration and inspiration valve, and said breathing system comprising at least tubing provided between the patient and the ventilator and a connector as well as possible other auxiliaries, the arrangement thus comprising a closing part, by means of which the connector can be closed during leak testing.

A ventilator can be defined briefly in the following manner. The purpose of a ventilator is to take care of the respiration of a patient and the change of gases when the patient's own spontaneous breathing is prevented. During anaesthesia, respiration is prevented due to administration of pharmaceuticals having a paralyzing effect on muscles and of anaesthetic gases. In intensive care, a patient may be connected to a ventilator to support spontaneous respiration.

The tubing by means of which breathing and anaesthetic gases are circulated between the lungs of a patient and an anaesthetic ventilator, and the bellows of the ventilator, valves, filters, directional valves, carbon dioxide absorber, a Y piece acting as a connector and possibly other auxiliaries associated with the tubing are referred to by a common term as a patient circuit or patient circulation.

As regards the patient circuit, it can be generally stated that the more connecting areas there are in the patient circuit, the greater is the likelihood of leaks.

Among the most common failures of equipments, taking place during anaesthesia and intensive care, are different leaks and detachments of tubes, the result of which may be, in the worst case, a prevention of the oxygen supply of the patient. Thus, a decrease in the oxygen content of blood, i.e. a hypoxia, is the most common cause of death related to anaesthetic accidents. The object of the automatic leak testing of the equipment is to prevent a hypoxia occurring during treatment, caused by internal leaks in the patient circuit, including the directional valves, absorbers and the Y piece, or in the ventilator.

However, it should be noted that a patient hazard can also be caused by an excess pressure in the patient circuit. Usually, a patient is connected to the patient circuit via an intubation tube and a Y piece, whereby the patient circulation and the lungs of the patient as well as the parts of the ventilator connected to the patient circulation have practically the same pressure. An increase in the pressure of the patient circuit is thus forwarded directly into the lungs, which expand as a result of the pressure. The expanding characteristics of lungs vary greatly between different patients; especially the lungs of child patients and those of patients whose lungs are seriously ill are inflexible, whereby the pressure rises rapidly dangerously high in the lungs of patients belonging to these patient groups. As a result of excess pressure, lung tissues may rupture or be otherwise damaged, whereby this may possibly result in intrapulmonary hemorrhages and even death in the worst case. Exactly corresponding damages may also be caused by excessive stretching of lungs due to excess pressure. In medicine, the exposure of lungs to excessive pressure is referred to by a term barotrauma.

To prevent leaks in a ventilator and the entire anaesthetic system, the equipment is checked thoroughly at least once a day, and a shorter check is carried out between operations, covering the patient circuit and other parts which are changed for hygiene reasons when a patient is replaced with another.

Leak testing is carried out daily manually when the equipment is started to be used by observing instructions drawn up by authorities or the hospital's own instructions, which are usually presented in the form of a checklist. The checklist may be a form attached to an anaesthetic record or a plastic-coated checklist hanging beside the apparatus, it being possible to erase entries made on said checklist before a new check begins.

In carrying out mechanical ventilation leak testing by means of a checklist, which may be for instance an FDA (Food and Drug Administration) format dating from 1992, an additional ventilation bag is first attached to the Y piece. The oxygen fresh gas flow is set to 250 ml/min, and the other fresh gas flows are closed. If an airway monitor adapter is connected to the circulation, it must be removed from the circulation before the test is started. Thereafter, the patient circuit is pressurized by using an emergency oxygen button, which causes a strong additional oxygen flow. The bellows of the ventilator rises to its upper position, and the breathing bag is filled with oxygen. The apparatus is allowed to ventilate for several respiratory cycles. At the same time, it is checked that the ventilator delivers the set batch volume to the bag during the inspiratory phase and that the bellows is filled in its entirety during the expiratory phase. If the bellows gradually starts to fill only partly, the patient circuit leaks.

Manual ventilation leak testing is carried out in the following manner. First, all fresh gas flows are closed. The APL valve is closed, and the connector, i.e. the Y piece, is stopped up with a finger. The patient circuit is pressurized to 30 cm $H_2O$ by using an emergency oxygen button. The pressure must remain at this level for at least 10 seconds.

As an example of solutions known in the field, Cicero anaesthetic work stations manufactured by Drägerwerk AG can be mentioned, in which testing is performed in connection with starting the apparatus, but it can also be performed between patients. A Cicero workstation is provided with a closing part to which the Y piece is connected for the duration of the leak test. The purpose of the test is to detect leaks in the piston-cylinder unit and the tubes of the patient circulation. It does not detect leaks in the reservoir tube and the fresh gas section. With the use of Cicero workstation, it should be noted that the test must not be performed when the apparatus is connected to a patient.

One of the disadvantages of the test of the above-mentioned apparatus is that it includes no safety mechanism which would prevent leak testing when the patient tubing is connected to a patient. The pressure can be adjusted to no more than 40 mbar, and the duration of the test to 20–25 seconds. As regards a normal adult patient, this pressure is not yet life-threatening, but for a child patient and for a person with a lung condition it is hazardously high. Another disadvantage is that it must be indicated to a Cicero workstation when the Y piece is stopped up and when it is not stopped up.

Another example of prior art is a solution where the basic principle is the same as in the above-mentioned solution based on an FDA checklist, but the difference is that some phases are automatized. Before a leak test is started, some procedures must be performed manually, however. The fresh gas flows must be closed. The laughing gas can be restricted by means of a solenoid valve, so that it could also be shut off automatically. On the other hand, the oxygen and air must be shut off manually. The system measures fresh gas proportions and detects when the fresh gas flows are approximately closed. The AUTO/MAN valve of this solution is manually operated, wherefore the user has to turn the valve to the correct position if it is not in the position required by the leak test. The system recognizes the position of the AUTO/MAN valve automatically. When the valve is in the correct position, the system acknowledges the valve as turned.

The disadvantage of the solution presented above is that the Y piece must be stopped up manually and that the user of the system must indicate to the software that the Y piece is stopped up, because the system is not capable of observing automatically if the Y piece is stopped up in the correct manner, i.e. if the closing part is used in the correct manner or not.

SUMMARY OF THE INVENTION

The object of the invention is to provide an arrangement by means of which the disadvantages associated with the prior art can be obviated. This is achieved with the arrangement of the invention, characterized in that the closing part is provided with a detecting means, which is arranged to provide a signal when the closing part closes the connector.

The main advantage of the invention is that by means of the invention it is possible to prevent a barotrauma from being produced in the lungs of a patient as a result of the pressurization of the patient circuit caused by the automatic leak testing of the apparatus. In addition, an advantage of the invention is its simplicity, since with the use of the invention there is no need for a complicated and expensive algorithm, which would try to reliably determine on the basis of the rise of the pressure whether the connector is really stopped up or whether it is in the air or whether it is connected to the patient.

BRIEF DESCRIPTION OF THE DRAWINGS

In the following, the invention will be described in more detail by means of the preferred embodiments shown in the accompanying drawing, in which.

DETAILED DESCRIPTION OF THE PREFERRED EMBODIMENT

Figure 1:
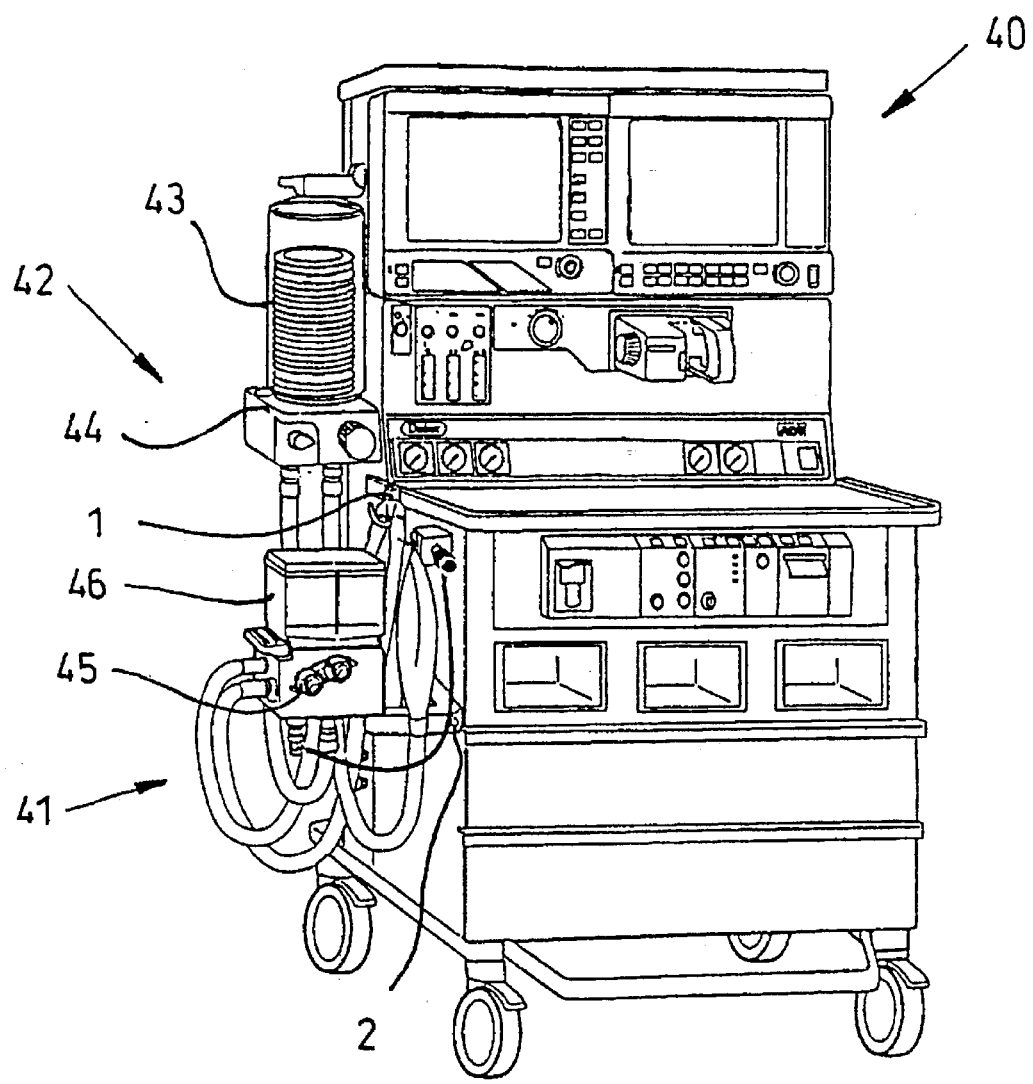
FIG. 1 shows a schematic view of equipment consisting of a ventilator and a patient circuit.

The present invention thus relates to an arrangement for leak testing an equipment consisting of a ventilator and of a breathing system provided between the ventilator and a patient. One such equipment is shown schematically in FIG. 1. This equipment is included as a part of an anaesthetic work station 40 of the example of FIG. 1. Breathing and anaesthetic gases are passed from the ventilator included in the anaesthetic work station 40 to the lungs of a patient by means of tubing 41. The ventilator comprises at least a as delivery means 42 connected with the tubing and an expiration and inspiration valve. The gas delivery means may be for instance a bellows 43. The expiration and inspiration valve may be one multi-purpose valve or two separate valves. The breathing system provided between the ventilator and the patient comprises at least the tubing 41 provided between the patient and the ventilator, and a connector 1. In addition, other possible auxiliaries are included in the system, for instance a bacterial filter, which may be located for instance at the connector 1, directional valves 45, and carbon dioxide absorber 46. The details presented above, the functions thereof, and the unit consisting of the details presented above represent completely known prior art to one skilled in the art, wherefore these matters are not dealt with in more detail in this context.

Figure 2:
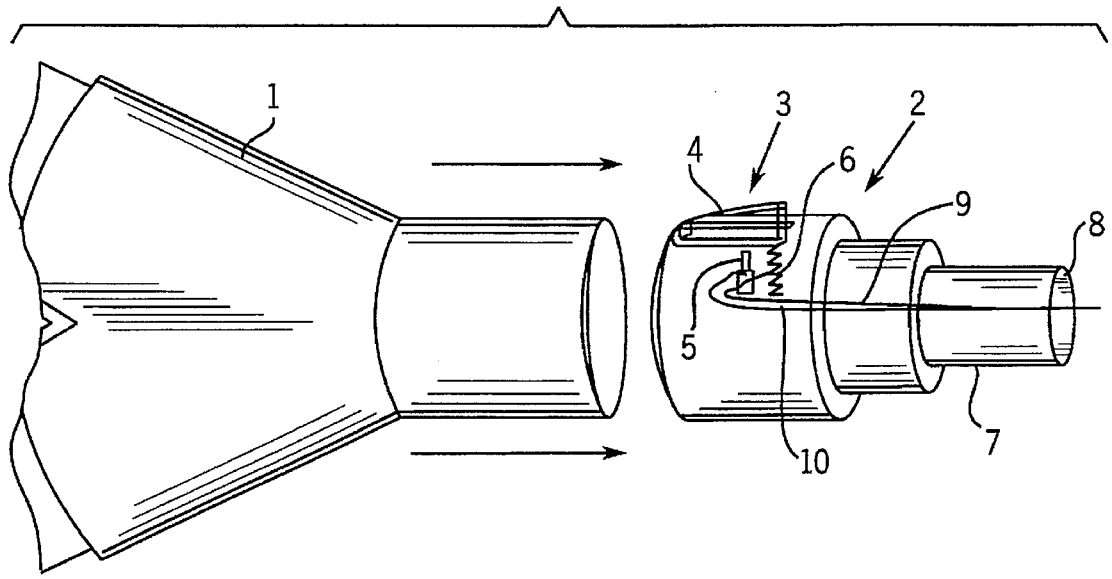
FIG. 2 shows a schematic view of a first embodiment of the arrangement of the invention.

A first embodiment of the arrangement of the invention is shown for the sake of clarity in FIG. 2 in such a manner that reference numeral 1 indicates only the connector by means of which a patient can be connected to the above-mentioned patient circuit. The connector 1 is also shown in FIG. 1. Reference numeral 2 indicates in a general manner a closing part by means of which the connector 1 can be closed during leak testing. The closing part 2 is also shown in FIG. 1. The connector may be for instance a Y piece. The closing part 2 may be for instance an essentially cylindrical piece, as shown in FIG. 2. Closing of the connector is performed by pushing the connector 1 so as to enclose the closing part, as shown by means of an arrow in FIG. 2.

According to the essential idea of the invention, the closing part 2 is provided with a detecting means 3, which is arranged to provide a signal when the closing part 2 closes the connector 1. In the embodiment of FIG. 2, the detecting means 3 comprises a moving part 4, which is arranged to move between a first position extending from the outer surface of the closing part 2 and a second position differing from the first position. The moving part may be for instance a button-like part or a wedgelike part, as shown in FIG. 2. The second position of the moving part 4, differing from the first position, may be for instance a position in which the moving part 4 has sunk essentially to the level of the surface of the closing part 2. However, it should be noted that the exemplifying solutions presented above are not the only possible applications, but according to the basic idea of the invention it is also entirely possible to dispose the closing part within an enclosure structure, whereby the detecting means can be arranged in the enclosure structure in such a manner that the connector fits, in a closing situation, in the space remaining between the closing part and the enclosure structure, whereby the moving part is capable of moving between the first and the second position in principle in the same manner as presented above. In such an application, the moving part may move to the second position for instance by the action of the outer surface of the connector when the closing part closes the connector.

The detecting means 3 also comprises a microswitch 5, which is arranged to indicate when the moving part 4 is in the second position. The microswitch 5 may be any component known as such. The moving part 4 is arranged to move to the first position extending from the outer surface of the closing part by the action of a spring 6 and, correspondingly, to move to the second position when the connector is pushed so as to enclose the closing part 2. According to FIG. 2, the moving part may be hinged at the outermost end of the closing part, the inner end thus resting on the spring 6, as shown in FIG. 2. The moving part 4 is thus arranged to move freely in the manner described above, depending on whether the connector 1 is attached to the closing part 2 or not.

The connection between the connector and the closing part must be rendered as tight as possible. It is thus preferable to arrange the moving part 4 in such a manner that it extends preferably to only less than half of the length of the closing part 2, as shown schematically in FIG. 2. The connector can thus be made to enclose the closing part 2 tightly.

The closing part 2 may be partly hollow, whereby the supporting structures of the microswitch 5 and of the spring 6 must be designed separately. The hollow structure must also be outwardly tight in order that the connector could be stopped up successfully. The closing part may also be a piece cast to shape, in which are included the supporting structures of the microswitch and of the spring as well as the hinge assembly of the moving part 4, whereby the structure can be kept tight more easily.

The arrangement which is in accordance with what is presented above is capable of detecting when the connector 1 is pushed over the closing part 2 and providing a signal of this to the testing system. The operation is fully automatic, i.e. no manual acknowledgement is required. The closing part 2 may generate the signal for instance in such a manner that the moving of the detecting means 3 to the second position at the level of the surface of the closing part 2 generates the signal. This can naturally also be implemented in such a manner that the moving of the detecting means 3 to the second position interrupts a certain continuous signal, the interruption of the continuous signal being thus actually the signal provided by the detecting means.

In FIG. 2, reference numeral 7 indicates a hollow tube to which the closing part 2 is attached. The tube 7 is secured at one of its ends, i.e. at the area indicated by reference numeral 8, to a suitable base, for instance to the side of a power ventilator or an anaesthetic equipment. Reference numerals 9 and 10 indicate conductors by means of which the microswitch 5 is connected to the binary inputs of the ventilator central unit.

Figure 3:
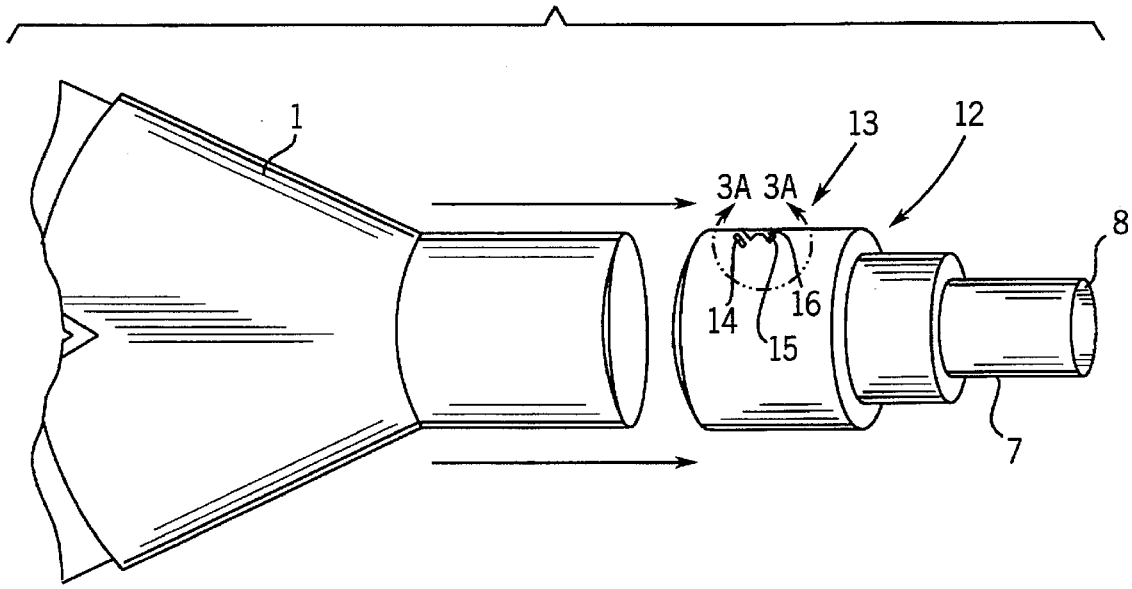
FIG. 3 shows a schematic view of a second embodiment of the arrangement of the invention.
Figure 3A:
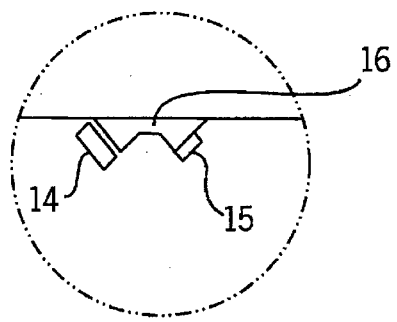
FIG. 3A is an enlarged, detailed view of a portion of the embodiment of the invention shown in FIG. 3.

FIGS. 3 and 3A show a second embodiment of the arrangement of the invention. In FIG. 3, areas corresponding to those in the example of FIG. 2 are indicated by the same reference numerals. In FIG. 3, reference numeral 12 denotes the closing part and reference numeral 13 denotes the detecting means. In this solution, detection is carried out optically by means of a sensor 14. A light source 15, which may be for instance a LED, is disposed in a shaped cavity 16 in such a manner that the light is not able to travel directly from the light source 15 to the sensor 14. When the connector 1 is pushed over the closing part 12, some light is reflected from the inner surface of the connector to the sensor 14. Naturally, the sensor 14 must be sensitive only to that wavelength which the light source 15 transmits.

Naturally, the embodiment described above can also be implemented in an opposite manner, i.e. in such a manner that the connector 1 pushed over the closing part hinders the light from travelling to the sensor. Thus, for instance a suitable enclosure structure surface is used, the light reflecting from this surface to the sensor when the connector 1 is not pushed over the closing part, etc. Obviously, the sensor can also be arranged in the above-mentioned enclosure structure, the sensor thus remaining outside the connector in a closing situation.

Figure 4:
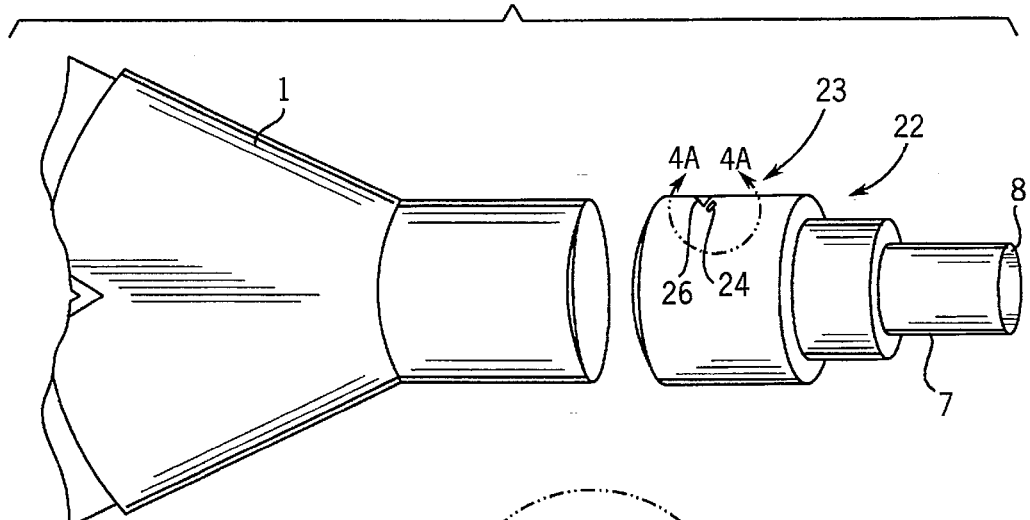
FIG. 4 shows a schematic view of a third embodiment of the arrangement of the invention.
Figure 4A:
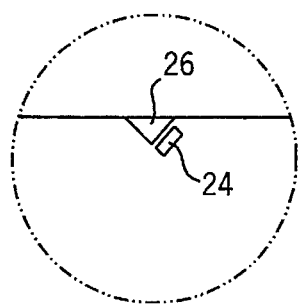
FIG. 4A is an enlarged, detailed view of a portion of the embodiment of the invention shown in FIG. 4.

FIGS. 4 and 4A show a third embodiment of the invention. In FIG. 4, areas corresponding to those in the examples of FIGS. 2 and 3 are indicated by the same reference numerals. In FIG. 4, reference numeral 22 denotes the closing part and reference numeral 23 denotes the detecting means. In this solution, surrounding light is utilized. A photo-sensitive sensor 24 is disposed in a suitably shaped cavity 26. The cavity 26 can be arranged for instance in the area of the tip of the closing part 22. It is preferable to arrange the cavity 26 to be directed slantingly upwards, as shown in FIG. 4A. When the connector 1 is pushed over the closing part 22, the surrounding light is not able to travel via the cavity 26 provided in the closing part 22 to the sensor 24.

This embodiment can also be implemented in an opposite manner, i.e. in such a manner that the connector pushed over the closing part allows surrounding light to travel to the sensor. The application can also be implemented as an enclosure structure, like the example of FIG. 3, the sensor thus remaining outside the connector in a closing situation.

Figure 5:
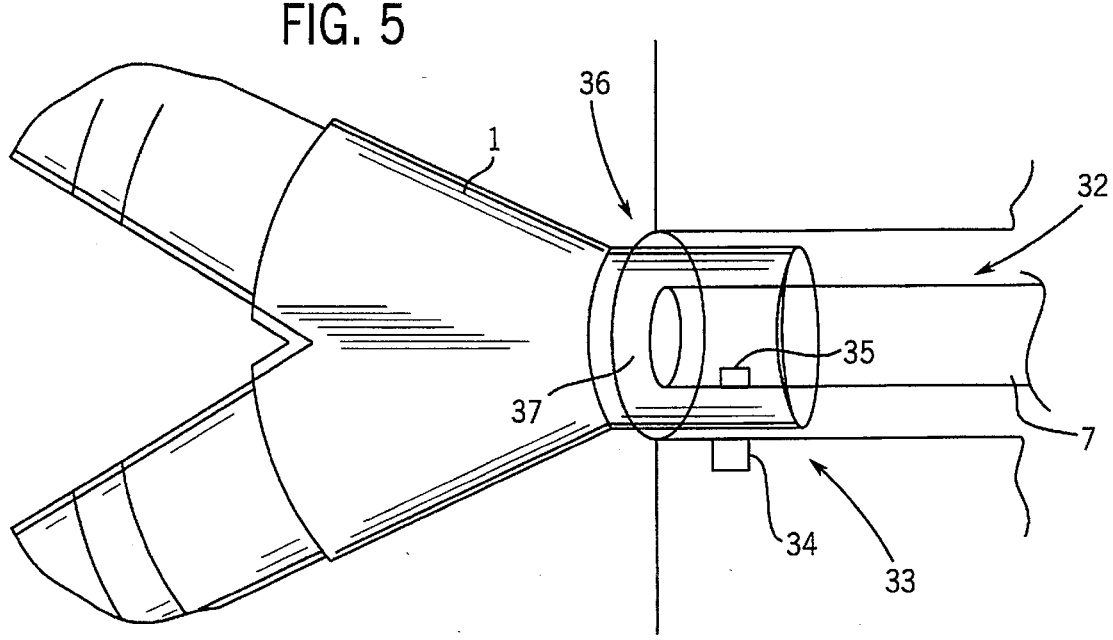
FIG. 5 shows a schematic view of a fourth embodiment of the arrangement of the invention.

FIG. 5 shows a fourth embodiment of the arrangement of the invention. In FIG. 5, areas corresponding to those in the examples of FIGS. 2–4 are indicated by the same reference numerals. In this embodiment, a closing part 32 is arranged within the enclosure structure of an apparatus. The apparatus may be for instance the anaesthetic equipment in connection of which the arrangement is used. In the embodiment of FIG. 5, a light source 35 arranged in the closing part 32 and a photo-sensitive sensor 34 arranged in the enclosure structure are used as a detecting means 33. The light source and the sensor can naturally also be arranged in an opposite manner. The light source 35 is disposed in the closing part as far from the opening 36 provided on the side of the enclosure structure as possible in order that the light entering through the opening would not disturb the detection. The outer dimensions of the opening 36 are of the order of the dimensions of the connector, and an intermediate space 37 is provided around the closing part 32 within the enclosure structure, this intermediate space enabling the connector 1 to be pushed over the closing part 32 in the manner according to FIG. 5. A collar made of a soft and flexible dark material can be provided around the opening 36, this collar preventing light from travelling to the sensor 34 through the opening 36. When the connector 1 is pushed in its place over the closing part, the connector prevents light from travelling from the light source 35 to the sensor 34. Naturally, the connector must be manufactured of such a material that the passage of light through the wall of the connector is prevented. The passage of light can be affected for instance by means of the colour of the material of the connector.

This application can also be implemented in an opposite manner, i.e. in such a manner that the connector pushed over the closing part allows light to travel to the sensor.

In the embodiments of FIGS. 3–5, the electric connections, wirings and other corresponding details can be implemented in principle in the same manner as presented in connection with the embodiment of FIG. 2.

The embodiments presented above are by no means intended to restrict the invention, but the invention may be modified within the scope of the claims quite freely. It will thus be apparent that the arrangement of the invention or the details thereof do not necessarily have to be exactly as presented in the figures, but also other types of solutions are possible. The closing part may also be for instance a conical piece, etc. Further, it is quite apparent that in the embodiment of FIG. 5 it is also possible to use a detecting means based on a microswitch or detecting means applications according to FIG. 3 or 4. Furthermore, the detection may be implemented in a capacitive manner, etc.

I claim:

1. An arrangement for leak testing equipment comprising a ventilator and a breathing system provided between the ventilator and a patient, said ventilator comprising a gas delivery means and an expiration and inspiration valve, and said breathing system comprising at least tubing provided between the patient and the ventilator and a connector, the arrangement comprising a closing part, by means of which the connector can be closed during leak testing, the closing part being provided with a detecting means, which is arranged to provide a signal when the closing part closes the connector.

2. An arrangement according to claim 1, wherein the detecting means comprises a moving part, which is arranged to move between a first position and a second position, the second position differing from the first position, and a microswitch, which is arranged to indicate when the moving part is in the second position.

3. An arrangement according to claim 2, wherein the closing part is arranged within an enclosure structure in such a manner that the enclosure structure surrounds the closing part at a distance as seen in the radial direction of the closing part, providing an intermediate space between the closing part and the enclosure structure.

4. An arrangement according to claim 2, wherein the moving part is a wedge-like part.

5. An arrangement according to claim 1, wherein the detecting means comprises an optical sensor and a light source, which are arranged in such a manner in relation to each other that the connector prevents or allows the light originating from the light source to travel to the optical sensor when the closing part closes the connector.

6. An arrangement according to claim 5, wherein the closing part is arranged within an enclosure structure in such a manner that the enclosure structure surrounds the closing part at a distance as seen in the radial direction of the closing part, providing an intermediate space between the closing part and the enclosure structure.

7. An arrangement according to claim 1, wherein the detecting means comprises an optical sensor, which is arranged in the closing part in such a manner that the connector prevents or allows surrounding light to travel to the optical sensor when the closing part closes the connector.

8. An arrangement according to claim 1, wherein the closing part is arranged within an enclosure structure in such a manner that the enclosure structure surrounds the closing part at a distance as seen in the radial direction of the closing part, providing an intermediate space between the closing part and the enclosure structure; and the detecting means comprising a light source and an optical sensor, one of which is arranged in the closing part and the other in the enclosure structure in such a manner that the connector pushed into the intermediate space between the closing part and the enclosure structure so as to enclose the closing part prevents or allows the light originating from the light source to travel to the optical sensor.

9. An arrangement according to claim 1, wherein the connector is a Y piece.

10. An arrangement according to claim 1, wherein the breathing system provided between the ventilator and the patient comprises a bacterial filter, directional valves, and a carbon dioxide absorber.

11. An arrangement according to claim 10, wherein the ventilator is an anaesthetic ventilator.

12. An arrangement according to claim 11, wherein breathing and anaesthetic gases are arranged to be circulated between the lungs of the patient and the anaesthetic ventilator by passing the gas leaving the lungs of the patient via at least the carbon dioxide absorber and the directional valves to the lungs of the patient.

13. An arrangement according to claim 10, wherein breathing and anaesthetic gases are arranged to be circulated between the lungs of the patient and the ventilator by passing the gas leaving the lungs of the patient via at least the carbon dioxide absorber and the directional valves to the lungs of the patient.

14. An arrangement according to claim 1, wherein the ventilator is an anaesthetic ventilator.

15. An arrangement according to claim 1, wherein breathing and anaesthetic gases are arranged to be circulated between the lungs of the patient and the ventilator by passing the gas leaving the lungs of the patient via at least a carbon dioxide absorber of the breathing system ahd the valve to the lungs of the patient.

* * * * *